US00PP30887P2

(12) United States Plant Patent
Fulcher

(10) Patent No.: US PP30,887 P2
(45) Date of Patent: Sep. 17, 2019

(54) ***AGAPANTHUS* PLANT NAMED 'PC 11107'**

(50) Latin Name: ***Agapanthus* hybrid**
Varietal Denomination: PC 11107

(71) Applicant: Richard John Fulcher, Chulmleigh (GB)

(72) Inventor: Richard John Fulcher, Chulmleigh (GB)

( * ) Notice: Subject to any disclaimer, the term of this patent is extended or adjusted under 35 U.S.C. 154(b) by 26 days.

(21) Appl. No.: 15/731,993

(22) Filed: Sep. 5, 2017

(51) Int. Cl.
*A01H 5/02* (2018.01)
*A01H 6/04* (2018.01)

(52) U.S. Cl.
USPC ..... Plt./398
CPC ..... *A01H 6/04* (2018.05)

(58) Field of Classification Search
USPC ..... Plt./398
See application file for complete search history.

(56) References Cited

PUBLICATIONS

UPOV hit on *Agapanthus* plant named 'PC 11107', QZ PBR 44518, filed Feb. 1, 2014.*

* cited by examiner

*Primary Examiner* — Anne Marie Grunberg
(74) *Attorney, Agent, or Firm* — Penny J. Aguirre

(57) ABSTRACT

A new cultivar of *Agapanthus* plant, 'PC 11107', that is characterized by its early flowering habit, its short plant height, its flowers that are bright, intense deep blue in color, its flower tepals that are broad, and its deciduous growth habit.

2 Drawing Sheets

Botanical classification: *Agapanthus* hybrid.
Varietal denomination: 'PC 11107'.

CROSS REFERENCE TO A RELATED APPLICATION

This application is related to a European plant breeders' rights application filed on Feb. 1, 2014, application No. 2014/0138. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Agapanthus* of hybrid origin and will be referred to hereafter by its cultivar name, 'PC 11107'. 'PC 11107' represents a new perennial herb grown for landscape use.

The new cultivar was discovered as a chance seedling by the Inventor at his nursery in Eggesford, England, United Kingdom in in June of 2011. The new cultivar was growing in a container amongst other seedlings derived from seed collected and pooled in 2008 pooled from various unpatented *Agapanthus* varieties in a collection. The parentage of 'PC 11107' is therefore unknown.

Asexual propagation of the new cultivar was first accomplished by rhizome division by the Inventor in Eggesford, England, United Kingdom in April of 2013. Asexual propagation by division and tissue culture has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'PC 11107' as a distinct cultivar of *Agapanthus*.

1. 'PC 11107' exhibits an early flowering habit.
2. 'PC 11107' exhibits a short plant height.
3. 'PC 11107' exhibits flowers that are bright, intense deep blue in color.
4. 'PC 11107' exhibits flower tepals that are broad.
5. 'PC 11107' exhibits a deciduous growth habit.

'PC 11107' can be most closely compared to the *Agapanthus* cultivars 'Brilliant Blue' (U.S. Plant Pat. No. 25,966) and 'Taw Valley' (not patented). 'Brilliant Blue' is similar to 'PC 11107' in having somewhat broad flower tepals. 'Brilliant Blue' differs from 'PC 11107' in having flower tepals that are less broad and in having an evergreen growth habit. 'Taw Valley' is similar to 'PC 11107' in having flowers that are dark blue in color. 'Taw Valley' differs from 'PC 11107' in having flowers that are darker blue in color and in having a taller plant height with arching stems.

BRIEF DESCRIPTION OF THE DRAWINGS

The accompanying colored photographs illustrate the overall appearance and distinct characteristics of the new *Agapanthus*. The photographs were taken of 14 month-old plants of 'PC 11107' as grown in the ground in Eggesford, England, United Kingdom.

The photograph in FIG. 1 provides a side view of a plant of 'PC 11107' in bloom.

Figure 1:
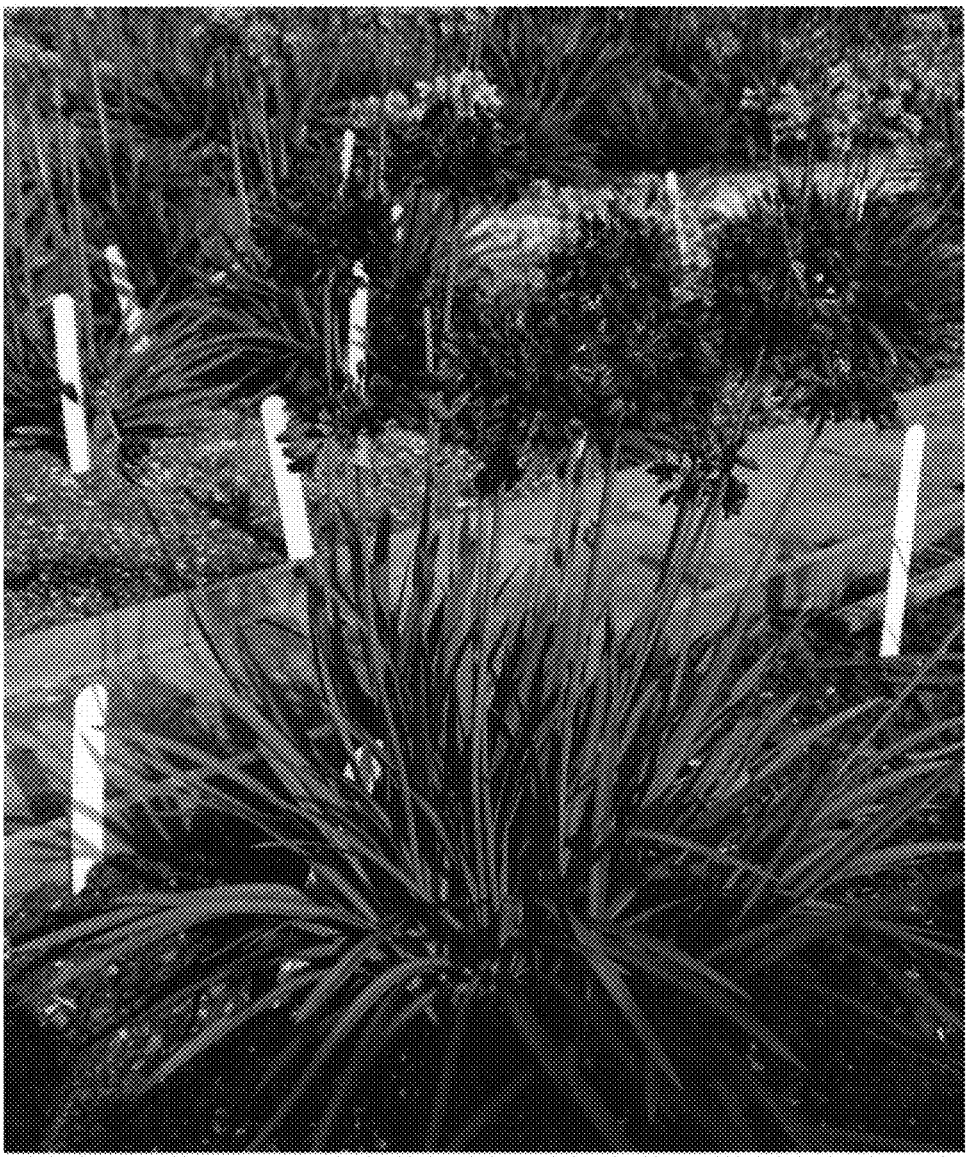
Figure 2:
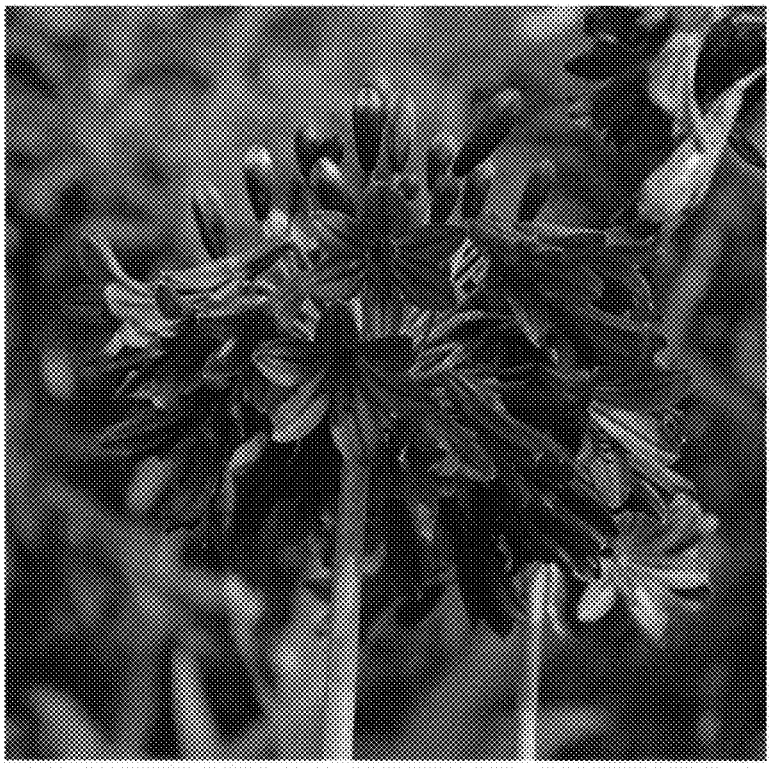

The photograph in FIG. 2 provides a close-up view of an inflorescence of 'PC 11107'.

Figure 3:
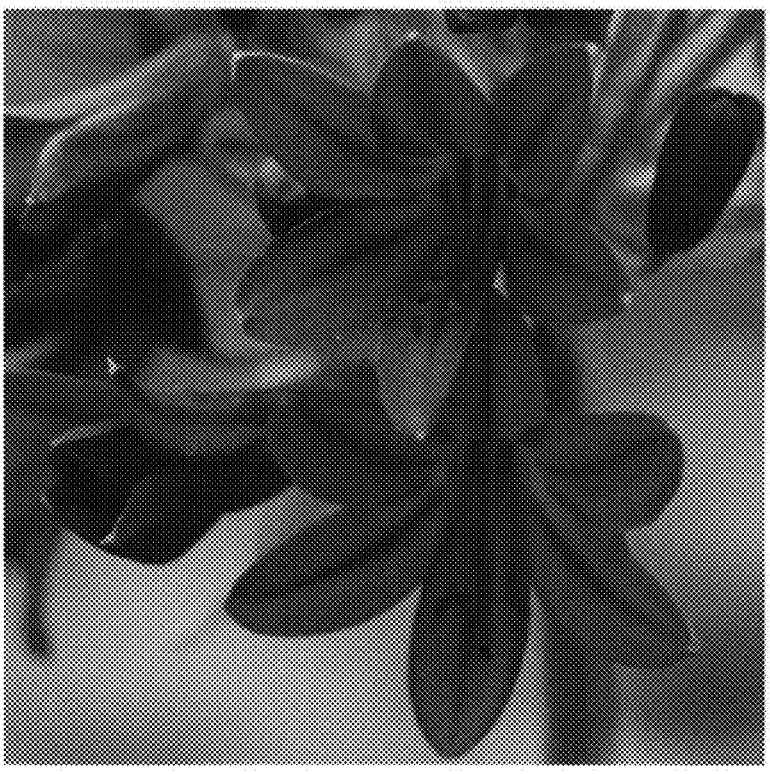

The photograph in FIG. 3 provides a close-up view of the flowers of 'PC 11107'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of plants two years in age as grown outdoors in Eggesford, England, United Kingdom. The phenotype of the new cultivar may vary with variations in environmental, climatic, and cultural conditions, as it has not been tested under all possible environmental conditions. The color determinations are in accordance with The 2015 R.H.S. Colour Chart of The Royal Horticultural Society, London, England, except where general color terms of ordinary dictionary significance are used.

General description:

*Blooming period.*—Early blooming; 6 to 7 weeks from the end of June to mid August in The United Kingdom.

*Plant type.*—Deciduous herbaceous perennial.

*Plant habit.*—Basal rosettes with inflorescences emerging from the rosette center, compact, short in height, upright stems, spreading.

*Height and spread.*—Average of 45 cm in height, 50 to 60 cm in spread.

*Cold hardiness.*—Hardy at least to United Kingdom Zone 4 in typical winters.

*Diseases and pests.*—No resistance or susceptibility to diseases or pest has been observed.

*Root description.*—Thick and fleshy, 161C in color.

*Propagation.*—Tissue culture and division.

*Growth rate.*—Moderate.

*Number of shoots (rosettes).*—An average of 16 as grown in the ground as a two year-old plant.

Foliage description:

*Leaf shape.*—Ligulate.

*Leaf division.*—Simple.

*Leaf base.*—Truncate.

*Leaf arrangement.*—2-ranked, arranged in shoots an average of 1 cm diameter at base.

*Leaf apex.*—Narrow acute.

*Leaf aspect (curvature).*—Emerging leaves erect, then lower leaves cascade.

*Leaf venation.*—Parallel, upper surface; matches leaf coloration with mid rib slightly lighter 138D, and lower surface; matches leaf coloration with mid 144A.

*Leaf margins.*—Entire.

*Leaf size.*—Up to 29 cm in length and up to 2.6 cm in width.

*Leaf surface.*—Smooth, glabrous, and dull on upper and lower surface.

*Leaf number.*—Average of 8 leaves per shoot.

*Leaf variegation.*—Absent.

*Leaf color.*—Young leaves, upper and lower surface; color between 138A and 144A and 145D at base, mature leaves upper and lower surface; 138A with base 145D.

*Leaf attachment.*—Sessile to base.

Flower description:

*Inflorescence type.*—Dense umbel.

*Flower fragrance.*—None.

*Flower type.*—Single, campanulate with base of tepals fused and spreading lobes.

*Flower number.*—30 to 60 flowers per umbel.

*Inflorescence size.*—Average of 6.5 cm in height and 14 cm in diameter.

*Inflorescence shape.*—Rounded to domed in lateral view.

*Flower size (comprised of perianth).*—3.5 to 6.4 cm in diameter, 3.0 to 3.5 cm in length with tube portion 1.2 to 1.5 cm in length.

*Lastingness of inflorescence.*—Average 7 days.

*Flower aspect.*—Upward to downward.

*Peduncle.*—1 per rosette, very strong, oval in shape and cross section, held primarily upright, average of 50 cm in length and 8 mm in width at apex and 1 cm in width at base, 138A to 138B in color with glaucous coating 138D with base 145B, surface glabrous and glaucous, anthocyanin absent.

*Pedicels.*—Very strong, average of 4 cm in length and 2.2 mm in width, held erect to outward (0° to 180°), a blend of 138B and 138C in color, glabrous and slightly glaucous surface, anthocyanin absent.

*Flower buds.*—Obelliptic in shape, average of 2.2 cm in length and 7 mm in width, a blend of 95B and 95C and blending with 95D towards apex.

*Inflorescence bracts.*—2 deciduous spathe-like bracts that split open on one side and drop when flowers open; ovate to lanceolate in shape, acuminate apex (1 cm in length), truncate base, up to 7 cm in length and 2.5 cm in width, color outer surface; 144A and suffused with 145D at base, color inner surface; 147B in color and striations of 147C, glabrous and dull on both surfaces, anthocyanin absent.

*Tepals.*—6 lobes, lobes oblanceolate in shape and slightly overlapping, lower 40% fused into tube, entire margins with weak undulation and same color as center of lobes or 95B, broadly acute apex, glabrous and satiny on inner and outer surfaces, thick substance, an average of 3.2 cm in length and 9 mm in width, color on both surfaces and inner and outer tube; a blend of 95C and 95D with center vein on inner surface of lobes 95B, midrib zone transparency absent, tube portion is an average of 2.5 cm in length and 7.5 mm in width.

Reproductive organs:

*Gynoecium.*—1 pistil, average of 2.3. cm in length, stigma is narrow clavate in shape and 95D in color, style is 1 cm in length and 95C and 95D in color, ovary is obelliptic in shape, 1 cm in length, 4 mm in width and 145D in color, pistillodes absent.

*Androcoecium.*—6 stamens, extruded but shorter than tepal length, anthers are dorsifixed, oblong in shape, average of 5 mm in length, and 146D in color, filament is 1.8 cm in length and 95C and 95D in color, pollen is moderately abundant in quantity and 18C in color, staminodes absent.

*Fruit/seed.*—Have not been observed.

It is claimed:

1. A new and distinct cultivar of *Agapanthus* plant named 'PC 11107' as herein illustrated and described.

* * * * *